United States Patent [19]

Bernardo

[11] Patent Number: 4,863,718

[45] Date of Patent: Sep. 5, 1989

[54] PROCESS FOR THE ELABORATION OF AN INSECTICIDE

[75] Inventor: Orlando Bernardo, Santos, Brazil

[73] Assignee: Casa Bernardo Ltd., Santos, Brazil

[21] Appl. No.: 777,532

[22] Filed: Sep. 19, 1985

[30] Foreign Application Priority Data

Sep. 19, 1984 [BR] Brazil .................................. 8404679
Sep. 19, 1984 [BR] Brazil .................................. 8404680

[51] Int. Cl.$^4$ ............................................. A01N 25/06
[52] U.S. Cl. ..................................... 424/40; 424/400;
424/405; 424/409; 424/601; 47/48.5; 47/57.5
[58] Field of Search .................... 424/128, 78, 40, 81,
424/154, 400, 405, 409; 47/48.5, 57.5

[56] References Cited

U.S. PATENT DOCUMENTS

| Re. 32,356 | 2/1987 | Cardarelli | 424/81 |
|---|---|---|---|
| 4,228,614 | 10/1980 | Cardarelli | 424/83 |
| 4,237,113 | 12/1980 | Cardarelli | 424/83 |
| 4,344,250 | 8/1982 | Fahlstrom | 47/48.5 |
| 4,400,374 | 8/1983 | Cardarelli | 424/78 |

*Primary Examiner*—Thurman K. Page
*Assistant Examiner*—P. J. Ryan

[57] ABSTRACT

An insecticide composition preferably composed of approximately 79% petroleum jelly, 20% aluminium phosphide in powder form and 1% additive catalyst and method of application, is disclosed. The composition is applied to orifices made by insects which attack fruit bearing trees, particularly orange-tree borers. The composition is characterized by the release of phosphine gas upon its exposure to air.

8 Claims, No Drawings

PROCESS FOR THE ELABORATION OF AN INSECTICIDE

The present invention relates to an insecticide composition, and particularly relates to a composition for the killing and elimination of coleoptera, including orange tree borers and other pests which plague fruit bearing trees by producing orifices in the branches and stalks of such trees, in particular citrus fruit bearing trees.

An object of this invention is to provide ann insecticide composition which releases an active ingredient upon exposure to air, and which is safe, easy and efficient to use.

SUMMARY OF THE INVENTION

The insecticide composition of the present invention comprises aluminum phosphide and petroleum jelly. The composition is applied to orifices made by insects which attack fruit producing trees. Upon exposure to air, the composition releases phosphine gas which kills the insects.

DETAILED DESCRIPTION

The insecticide composition of the present invention comprises aluminum phosphide (AlP) mixed with a medium having a doughy consistency. Advantageously the medium is petroleum jelly.

Advantageously the insecticide composition additionally contains an appropriate additive which acts as a catalyst to facilitate the release of phosphine gas when the insecticide composition comes into contact with air.

The insecticide composition utility stems from the reaction between aluminum phosphide and the water in the air (humidity) according to the following reactions:

$$AlP + 3H_2O \rightarrow PH_3 + Al(OH)_3$$ 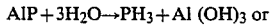 or $$2AlP + 3H_2O \rightarrow 2PH_3 + Al_2O_3$$ 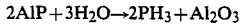

It is not necessary to expose the insecticide composition to water vapor; the humidity in the air is sufficient to release the phosphine gas ($PH_3$).

Advantageously the insecticide composition has 79% petroleum jelly of sufficient density to give the composition a paste-like consistency, 20% aluminum phosphide in powder form, and 1% additive. Advantageously the density of the composition is 1.12 g/cm$^3$.

Upon application of the composition according to this invention into the orifices created by the insects or larvae, phosphine gas is released into the orifices. Any coleoptera which are present in the orifices will die and become desicated. In addition, the paste-like consistency of the insecticide composition blocks the surface of the orifice so that the phosphine gas has a longer residence time inside the orifice, and the efficiency of the insecticide is effectively improved. Any harmful effects to the user are minimized.

It is possible to use a medium other than petroleum jelly in the insecticide composition which has similar physical characteristics. Petroleum jelly however, is considered to be the most advantageous.

Among the pests which may be exterminated by use of the insecticide composition according to the invention are the following:

Trachyderes Thoracicus—which are know to attack branches and trunks of trees;
Macropophora accentifer—which are known to attack stalks; and
Disploschema rotundicole—which are known to attack branches and stalks.

According to another embodiment of the invention, the composition is provided in an aluminum container (generally cylindrical) which can be quickly sealed, for example, with a threaded closure to avoid the release of phosphine gas outside of the orifices.

The effectiveness of the insecticide composition is preserved by storing it in a container where exposure to the air is minimized. Advantageously the container should be made of aluminum which is resistant to the aluminum phosphide.

The present invention also relates to a method of controlling pests comprising the step of applying a composition as above described into orifices which are bored into trees by the pests. Advantageously, 3 to 5 grams of the composition (using the advantageous proportions noted above) is applied per bored orifice.

It is to be understood that the relative percentages of petroleum jelly, aluminum phosphide and additive in the composition, and the amount of insecticide composition applied per orifice may vary considerably depending upon the problem presented.

Although over a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An insecticide composition for killing insects which bore orifices in trees comprising: a mixture of aluminum phosphide and a paste-like medium for application of said composition into the orifices, said composition upon being exposed to atmospheric moisture releases phosphine gas.

2. An insecticide composition according to claim 1 wherein said medium is petroleum jelly.

3. An insecticide composition according to claim 1 comprising approximately 79% petroleum jelly and 20% aluminum phosphide.

4. An insecticide composition according to claim 1 wherein the aluminum phosphide is in powder form.

5. An insecticide composition according to claim 1 which is provided in an aluminum container which is capable of being sealed airtight.

6. A method of controlling pests which bore orifices in trees comprising the step of applying an insecticide composition into the orifices comprising aluminum phosphide and in a paste consistency medium which releases phosphine gas when the composition comes into contact with air.

7. A method as in claim 6 wherein the applying step includes applying a mixture of approximately 79% petroleum jelly and 20% aluminum phosphide.

8. A method according to claim 7 wherein the applying step includes applying 3 to 5 grams of the insecticide composition per orifice.

* * * * *

UNITED STATES PATENT AND TRADEMARK OFFICE
CERTIFICATE OF CORRECTION

PATENT NO.  :  4,863,718

DATED       :  September 5, 1989

INVENTOR(S) :  Orlando Bernardo

It is certified that error appears in the above-identified patent and that said Letters Patent is hereby corrected as shown below:

Column 1, line 12:   "ann", should read   -- an --, line 31:   delete "which acts as a catalyst".

Signed and Sealed this

Thirteenth Day of April, 1993

*Attest:*

STEPHEN G. KUNIN

*Attesting Officer*       *Acting Commissioner of Patents and Trademarks*